US008666137B2

United States Patent
Nielsen et al.

(10) Patent No.: US 8,666,137 B2
(45) Date of Patent: Mar. 4, 2014

(54) APPARATUS AND METHOD FOR PROCESSING PROJECTION DATA

(75) Inventors: Tim Nielsen, Hamburg (DE); Thomas Koehler, Norderstedt (DE); Bernhard Brendel, Norderstedt (DE)

(73) Assignee: Koninklijke Philips N.V., Eindhoven (NL)

( * ) Notice: Subject to any disclaimer, the term of this patent is extended or adjusted under 35 U.S.C. 154(b) by 105 days.

(21) Appl. No.: 13/390,525

(22) PCT Filed: Sep. 1, 2010

(86) PCT No.: PCT/IB2010/053916
§ 371 (c)(1),
(2), (4) Date: Feb. 15, 2012

(87) PCT Pub. No.: WO2011/027298
PCT Pub. Date: Mar. 10, 2011

(65) Prior Publication Data
US 2012/0148136 A1 Jun. 14, 2012

(30) Foreign Application Priority Data
Sep. 7, 2009 (EP) .................................... 09169583

(51) Int. Cl.
*G06T 5/00* (2006.01)
(52) U.S. Cl.
USPC ........................................................ 382/131
(58) Field of Classification Search
None
See application file for complete search history.

(56) References Cited

U.S. PATENT DOCUMENTS

| 6,915,005 | B1 | 7/2005 | Ruchala et al. |
| 7,042,974 | B2 | 5/2006 | Goodgame et al. |
| 2004/0022348 | A1* | 2/2004 | Heumann ..................... 378/4 |
| 2006/0000983 | A1* | 1/2006 | Charron et al. .............. 250/394 |
| 2007/0242794 | A1* | 10/2007 | Stanton et al. .................... 378/5 |
| 2007/0248255 | A1 | 10/2007 | Chen |
| 2008/0240335 | A1 | 10/2008 | Manjeshwar et al. |
| 2009/0074278 | A1 | 3/2009 | Beaulieu et al. |

OTHER PUBLICATIONS

Ens, S., et al.; Sinogram-based Motion Detection in Transmission Computed Tomography; 2008; IFMBE Proceedings; pp. 505-508.
Kak, A. C., et al.; Principles of Computerized Tomographic Imaging; 1999; IEEE Press; electronic copy; pp. 1-4. http://www.slaney.org/pct.
Kyme, A. Z., et al.; Practical Aspects of a Data-driven Motion Correction Approach for Brain SPECT; 2003; IEEE Trans. on Medical Imaging; 22(6)722-729.

* cited by examiner

*Primary Examiner* — Jon Chang (57) ABSTRACT

The invention relates to a projection values processing apparatus (1) for processing acquired projection values. A first image is reconstructed from acquired projection values under consideration of a reconstruction assumption by a reconstruction unit (13). A simulated projection values determining unit (14) determines simulated projection values by simulating a projection through the reconstructed first image under consideration of the reconstruction assumption, and inconsistency values are determined for the acquired projection values by an inconsistency determining unit (15), wherein an inconsistency value is indicative of a degree of inconsistency of a respective acquired projection value with the reconstruction assumption, by comparing the acquired projection values and the simulated projection values. The inconsistency values can be used for different purposes, for example, improving the quality of a reconstructed image or indicating image elements being affected by an inconsistency between reconstruction assumption and acquired projection values.

17 Claims, 6 Drawing Sheets

APPARATUS AND METHOD FOR PROCESSING PROJECTION DATA

FIELD OF THE INVENTION

The invention relates to a projection values processing apparatus, a projection values processing method and a corresponding computer program for processing acquired projection values. The invention relates further to an imaging system for imaging a region of interest comprising the projection values processing apparatus.

BACKGROUND OF THE INVENTION

It is disclosed in, for example, "Principles of Computerized Tomographic Imaging", Kak, Slaney, IEEE Press, 1999, that a computed tomography system comprises an X-ray source for generating X-rays and a detector. The X-ray source and the detector rotate around a region of interest while the X-rays generated by the X-ray source traverse through the region of interest and are detected by the detector for acquiring projection data. An image of the region of interest is reconstructed by using a reconstruction algorithm which, for example, filters and backprojects the acquired projection data. The reconstructed images generally show image artifacts.

SUMMARY OF THE INVENTION

It is an object of the present invention to provide a projection values processing apparatus for processing acquired projection values, which provides means for improving the quality of an image which is reconstructed from the acquired projection values. It is a further object of the present invention to provide a corresponding projection values processing method and computer program. It is a further object of the present invention to provide a corresponding imaging system for imaging a region of interest, which comprises the projection values processing apparatus.

In a first aspect of the present invention a projection values processing apparatus for processing acquired projection values is provided, wherein the projection values processing apparatus comprises:
an acquired projection values providing unit for providing acquired projection values,
a reconstruction unit for reconstructing a first image from the acquired projection values under consideration of a reconstruction assumption,
a simulated projection values determining unit for determining simulated projection values by simulating a projection through the reconstructed first image under consideration of the reconstruction assumption,
an inconsistency determining unit for determining inconsistency values for the acquired projection values, wherein an inconsistency value is indicative of a degree of inconsistency of a respective acquired projection value with the reconstruction assumption, by comparing the acquired projection values and the simulated projection values.

The reconstruction of an image from acquired projection values is an inverse problem. A mathematical model which tries to predict the acquired projection values is given. This model can be regarded as a forward model and can be used by the simulated projection values determining unit for determining the simulated projection values. This model depends on variables like voxel values in a region of interest and constants which are not modified during reconstruction. In order to reconstruct an image, the reconstruction variables like the voxel values are determined based on the acquired projection values and by using the constant reconstruction parameters. The constant reconstruction parameters are the reconstruction assumptions. Thus, the reconstruction of an image from acquired projection data is based on reconstruction variables and reconstruction assumptions, wherein the reconstruction variables are optimized during the reconstruction process and anything else that is part of the above described model is a reconstruction assumption.

For example, if the acquired projection values have been acquired by a computed tomography apparatus, a reconstruction assumption is the acquisition geometry. Another reconstruction assumption can be the suppression of scattering in an object to be reconstructed, no inter pixel cross-talk in a detector which has been used for acquiring the projection values, correction of X-ray beam intensity variations, correction of beam hardening et cetera, i.e., for example, it can be assumed that X-ray beam intensity variations and/or beam hardening are not present. These reconstruction assumptions lead to a model in which the acquired projection values are expressed as line integrals through an object which can be characterized by a monoenergetic absorption coefficient. A further reconstruction assumption can be that there are no temporal variations of the object to be reconstructed during the acquisition of the projection values.

If the reconstruction assumptions are not good enough, i.e. if they do not fit to reality, the reconstructed image is not consistent with the acquired projection values. The inconsistency determining unit is adapted to determine inconsistency values which are indicative of the degree of this inconsistency between the acquired projection values and the reconstruction assumptions. These inconsistency values can be used for improving the quality of reconstructing an image from the acquired projection values. For example, the reconstruction assumptions can be modified and the inconsistency values can be determined again with respect to the modified reconstruction assumptions. If the inconsistency values are smaller with respect to the modified reconstruction assumption, the modified reconstruction assumption can be used for reconstructing an image from the acquired projection values for reducing artifacts in the reconstructed image caused by inconsistencies between the acquired projection values and the reconstruction assumptions. Thus, by determining the inconsistency values means for improving the quality of an image, which is reconstructed based on the acquired projection values, are provided.

The acquired projection values are preferentially projection values of a computed tomography imaging system or an X-ray C-arm system. The acquired projection values can also be projection values acquired by another imaging modality like a nuclear imaging system, for example, a positron emission tomography imaging system or a single photon emission computed tomography imaging system.

The acquired projection values providing unit is preferentially a storing unit in which the acquired projection values are stored or an acquired projection values receiving unit for receiving acquired projection values via a wireless or wired data connection and for providing the received acquired projection values. If the acquired projection value providing unit is a storing unit or an acquired projection values receiving unit, the projection values processing apparatus is preferentially comprised of a computer system including at least the reconstruction unit, the simulated projection value determining unit, the inconsistence determining unit and the acquired projection value providing unit.

As already mentioned above, the reconstruction assumption can be the acquisition geometry. The acquisition geometry is, for example, defined by the projection angle under which the projection values are acquired, the intensity of radiation used for generating the projection values, the degree of divergence of the radiation used for generating the projection values, wherein the degree of divergence can be parameterized by a cone angle and a fan angle, et cetera.

The reconstruction unit is preferentially adapted to perform a filtered back projection for reconstructing the first image of the object.

The simulated projection value determining unit is preferentially adapted to simulate a forward projection through the reconstructed first image under consideration of the reconstruction assumptions for determining the simulated projection values according to the reconstruction assumptions.

Preferentially, for each acquired projection value a simulated projection value is determined, and for each acquired projection value, i.e. for each pair of acquired projection value and corresponding simulated projection value, an inconsistency value is determined.

It is preferred that the inconsistency determining unit comprises a difference determining unit for determining differences between the acquired projection values and simulated projection values, wherein the inconsistency determining unit is adapted to determine the inconsistency values for the acquired projection values based the determined differences.

It is further preferred that the difference determining unit is adapted to determine the differences such that a high-frequency component of the differences is more suppressed than a low-frequency component of the differences. Preferentially, the high-frequency component is suppressed more than the low-frequency component by suppressing the high-frequency component but not the low-frequency component.

In order to allow the reconstruction unit to reconstruct an image, all quantities that are used by the respective reconstruction algorithm have to be provided as discrete values, i.e. all quantities are represented by a finite set of numbers. This use of discrete values yields discretization effects, i.e. even if the inconsistency would be zero, the acquired projection values and the simulated projection values which are simulated under consideration of the reconstruction assumption, would be different because of the discretization errors. These discretization errors adversely affect the inconsistency values in high spatial frequencies, i.e. in spatial frequencies being higher than spatial frequencies containing the structural information within the region of interest which has to be imaged. A determination of the differences such that a low frequency component of the difference is more pronounced than a high-frequency component, can therefore suppress the discretization errors in the determined differences and, thus, in the determined inconsistency values. This improves the quality of the inconsistency values.

The terms "low-frequency component" and "high-frequency component" relate to spatial frequencies.

Differences between acquired projection values and simulated projection values generally comprise a range of spatial frequencies, in particular, they comprise low-frequency components having spatial frequencies being lower than the spatial frequencies of high-frequency components. The inconsistency determining unit is preferentially adapted to determine the differences such that the high-frequency component is suppressed, i.e. to determine the differences such that a frequency component having a spatial frequency being larger than other frequency components of the differences is suppressed.

The frequency range in which the discretization errors are present depends on the discretization used during reconstructing an image and simulating the projection for determining simulated projection values. Since this used discretization is known, the frequency range of the discretization errors can be determined. The inconsistency determining unit is preferentially adapted to determine the differences such that high-frequency components, i.e. frequency components within the determined frequency range which is related to the discretization errors, are suppressed.

It is further preferred that the difference determining unit is adapted to low-pass filter the acquired projection values and to determine the differences by subtracting the respective low-pass filtered acquired projection value and the simulated projection value corresponding to the respective acquired projection value from each other.

The discretization effects lead to a loss of high-frequency components in the simulated projection values. Thus, if acquired projection values and simulated projection values are subtracted from each other, the subtraction result will show discretization errors in high-frequency components. If before subtracting the acquired projection values and the simulated projection values from each other also in the acquired projection values the high-frequency components are suppressed, the subtraction result has less discretization errors in the high-frequency components. This improves the quality of the inconstancy values determined based on the subtraction result.

It is further preferred that the difference determining unit is adapted to determine the differences by subtracting the respective acquired projection value and the simulated projection value corresponding to the respective acquired projection value from each other for generating subtraction results and by low-pass filtering the subtraction results.

Since the differences are determined as low-pass filtered subtraction results, the high-frequency components which are caused by the discretization errors are suppressed or removed by the low-pass filter. Also this improves the quality of the inconsistency values.

It is further preferred that the difference determining unit is adapted to determine the differences by subtracting the respective acquired projection value and the simulated projection value corresponding to the respective acquired projection value from each other for generating subtraction results, by reconstructing a subtraction image from the subtraction results determined for the acquired projection values, and by simulating a projection through the reconstructed subtraction image.

The discretization during reconstructing an image and simulating the projection for determining simulated projection values leads to a suppression of high-frequency components. Thus, if the subtraction results are used for reconstructing a subtraction image and if a projection through the reconstructed subtraction image is simulated, the simulation results are subtraction results in which high-frequency components are suppressed, in particular, removed, thereby suppressing, in particular, removing discretization errors in the inconsistency values which are determined based on the subtraction results. Moreover, the discretization errors have been generated by the process of reconstructing the first image and determining the projection values by simulating a projection through the reconstructed first image, wherein the suppression of the high-frequency components, i.e. the suppression of the discretization errors, is performed by the same process. The suppression of the high-frequency components is therefore very well adapted to the discretization errors in the high-frequency components of the subtraction results. This further improves the quality of the inconsistency values.

It is further preferred that the inconsistency determining unit further comprises a noise weighting unit for determining a noise value for an acquired projection value, and for weighting the determined difference with the inverse of the determined noise value, wherein the inconsistency determining unit is adapted to determine the inconsistency value for an acquired projection value based on the weighted difference.

By weighing the determined differences with the inverse noise values, the differences are normalized with respect to the noise values. This further improves the quality of the inconsistency values, in particular, the comparability of inconsistency values belonging to different acquired projection values.

It is further preferred that the inconsistency determining unit is adapted to square the weighted difference and to determine an inconsistency value based on the squared weighted difference.

It is further preferred that the acquired projection values have been assigned to acquisition times, wherein the projection values processing apparatus further comprises a temporal inconsistency signal determining unit for determining a temporal inconsistency signal indicative of an inconsistency between an acquired projection value and the reconstruction assumption at different times by assigning the acquisition times to the inconsistency values determined for the acquired projection values of the respective acquisition time.

If the reconstruction unit is adapted to consider a stationary object as reconstruction assumption and if the object moves, the temporal inconsistency signal can be regarded as temporal motion signal indicating the motion of the object.

Preferentially, the temporal inconsistency signal determining unit is adapted to average the inconsistency values belonging to the same acquisition time to generate a one-dimensional temporal inconsistency signal.

It is further preferred that the reconstruction unit is adapted to reconstruct a second image based on the acquired projection values and the determined temporal inconsistency signal. This allows reconstructing a second image having reduced image artifacts caused by inconsistencies between the acquired projection values and the reconstruction assumption.

For example, the reconstruction unit can be adapted to reconstruct an image based on acquired projection values only, which have been acquired at a time at which the temporal inconsistency signal shows an inconsistency below a threshold. The reconstruction unit can also be adapted to use acquired projection values for reconstructing the second image, which have been acquired at times at which the temporal inconsistency signal shows an inconsistency within a predefined inconsistency range. This allows to reconstruct an image based on acquired projection values having a similar inconsistency.

It is further preferred that the projection values processing apparatus further comprises an inconsistency image determining unit for generating an inconsistency image, wherein for an image element of the inconsistency image inconsistency values which contribute to the respective image element are added. The inconsistency values which are used for generating the inconsistency image are preferentially the differences which have been determined by subtracting the acquired projection values and the simulated projection values from each other, wherein the differences are determined such that high-frequency components are suppressed, in particular, removed, from the subtraction results.

Such an inconsistency image can, for example, be used by a radiologist for indicating which parts of a reconstructed image should not be used for diagnostic purposes.

The summation of inconsistency values which contribute to a respective element of the inconsistency image is preferentially performed by an unfiltered back projection.

In an exemplarily embodiment, for determining a suitable low-pass filter for filtering the acquired projection data or the inconsistency values an inconsistency image showing structures, which are known to be caused by discretization errors, can be used. Such an inconsistency image can be determined by simulation. In this exemplarily embodiment, the low-pass filter can be chosen such that the structures, which are known to be caused by the discretization errors, are reduced.

An inconsistency value contributes to a certain image element, if the acquired projection value for which the respective inconsistency value has been determined is caused by a ray passing a position within the object represented by the certain image element.

It is further preferred that the reconstruction unit is adapted to reconstruct a second image of the object based on the acquired projection values and the determined inconsistency image for reducing image artifacts caused by inconsistencies between the acquired projection values and the reconstruction assumption.

It is further preferred that the projection values processing apparatus further comprises an overlaying unit for overlaying the reconstructed first image and the inconsistency image.

This allows directly showing to a user which parts of the first image are affected by image artifacts caused by inconsistencies of the acquired projection values. The inconsistency image can also be used to be overlaid over other images like the mentioned second image.

It is further preferred that the reconstruction unit is adapted to reconstruct a second image of the object from the acquired projection values and the determined inconsistency values for reducing image artifacts caused by inconsistencies between the acquired projection values and the reconstruction assumption.

For example, the reconstruction assumption can be modified such that the determined inconsistency values are reduced, in particular, minimized, wherein a final image is reconstructed from the acquired projection values under consideration of the modified reconstruction assumption. This improves the quality of the reconstructed final image.

It is further preferred that the reconstruction unit is adapted to determine acquired projection values having an inconsistency value below a predefined threshold and to use only the determined acquired projection values having an inconsistency value below the predefined threshold while reconstructing the second image.

Since acquired projection values showing a large inconsistency are not used for reconstructing the image, the quality of the reconstructed image can be improved.

It is further preferred that the reconstruction unit is adapted to determine acquired projection values having similar inconsistency values and to reconstruct an image of the object from the acquired projection values having similar inconsistency values.

Similar inconsistency values can indicate similar states of the object. Thus, by reconstructing an image of the object from acquired projection values having similar inconsistency values, an image of the object can be reconstructed which corresponds to a certain state of the object. For example, if the reconstruction assumption is that the object is not moving, similar inconsistency values can indicate similar moving states. In this case, by reconstructing an image of the object from acquired projection values having similar inconsistency values, an image of the object in a certain moving state can be reconstructed.

In a further aspect of the present invention an imaging system for imaging a region of interest is presented, wherein the imaging system comprises:
- a projection values acquisition unit for acquiring projection values of the region of interest, and
- a projection values processing apparatus for processing acquired projection values as defined herein.

In a further aspect of the present invention a projection values processing method for processing acquired projection values is provided, wherein the projection values processing method comprises following steps:
- providing acquired projection values,
- reconstructing a first image from the acquired projection values under consideration of a reconstruction assumption,
- determining simulated projection values by simulating a projection through the reconstructed first image under consideration of the reconstruction assumption,
- determining inconsistency values for the acquired projection values, wherein an inconsistency value is indicative of a degree of inconsistency of a respective acquired projection value with the reconstruction assumption, by comparing the acquired projection values and the simulated projection values.

In a further aspect of the present invention an imaging method for imaging a region of interest is presented, wherein the imaging method comprises following steps:
acquiring projection values of the region of interest, and
processing acquired projections values as defined herein.

In a further aspect of the present invention a computer program for processing acquired projection values is provided, wherein the computer program comprises program code means for causing a projection values processing apparatus as defined in claim 1 to carry out the steps of the projection values processing method as defined herein, when the computer program is run on a computer controlling the projection values processing apparatus.

In a further aspect of the present invention a computer program for imaging a region of interest is provided, wherein the computer program comprises program code means for causing an imaging system as defined herein to carry out the steps of the imaging method, when the computer program is run on a computer controlling the imaging system.

It shall be understood that the projection values processing apparatus, the imaging system, the projection values processing method, the imaging method, the computer program for acquiring acquired projection values and the computer program for imaging a region of interest have similar and/or identical preferred embodiments as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
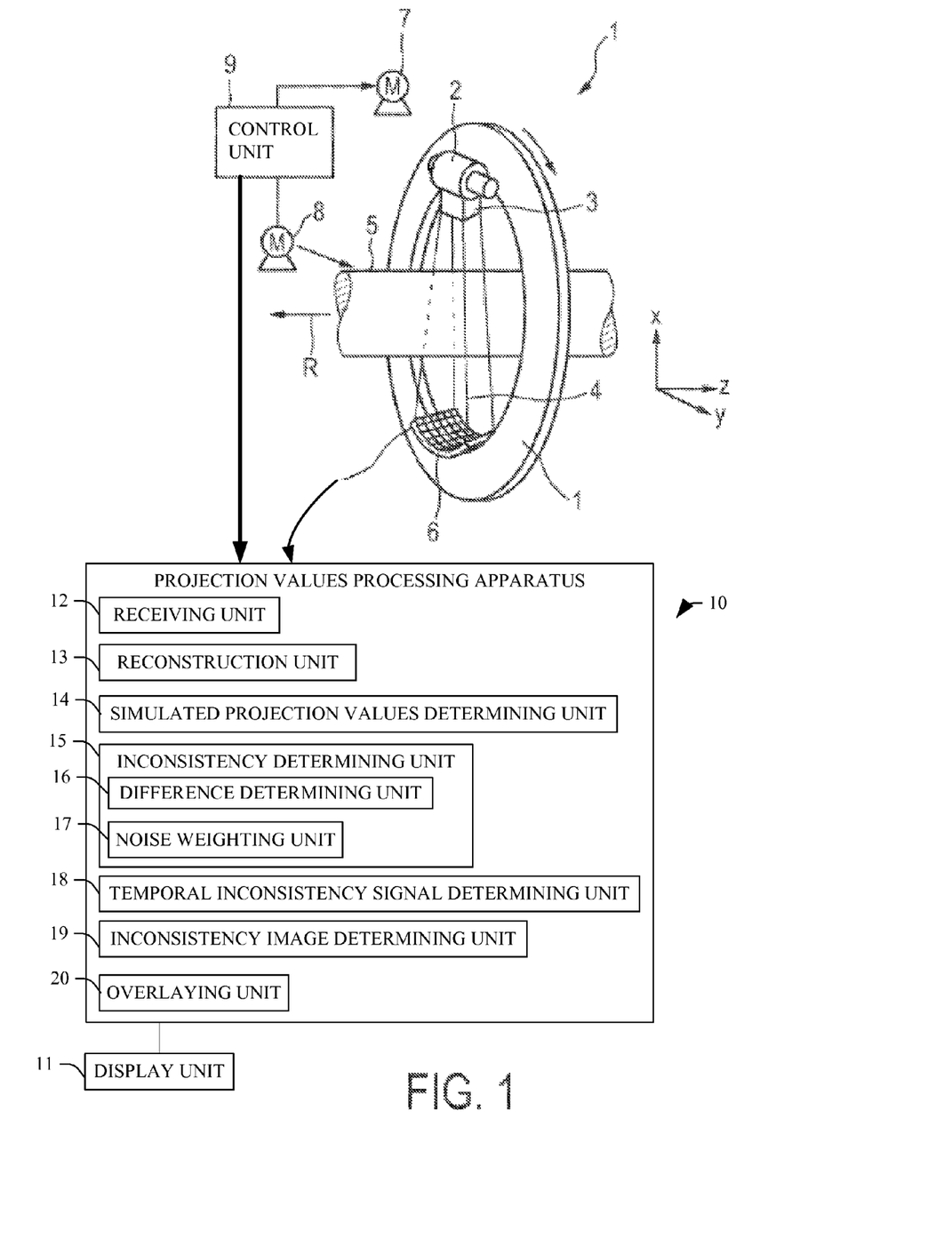
FIG. 1 shows schematically and exemplarily an imaging system for imaging a region of interest comprising a projection values processing apparatus.

FIG. 1 shows schematically and exemplarily an imaging system for imaging a region of interest being a computed tomography system. The computed tomography system includes a gantry 1 which is capable of rotation about a rotational axis R which extends parallel to the z direction. A radiation source 2, which is, in this embodiment, an X-ray tube, is mounted on the gantry 1. The radiation source 2 is provided with a collimator 3, which forms, in this embodiment, a conical radiation beam 4 from the radiation generated by the radiation source 2. The radiation traverses an object (not shown), such as a patient, and a region of interest, which is preferentially located within the object, in an examination zone, which is, in this embodiment, cylindrical. After having traversed the examination zone 5 the radiation beam 4 is incident on a detection device 6, which comprises a two-dimensional detection surface. The detection device 6 is mounted on the gantry 1.

The computed tomography system comprises two motors 7, 8. The gantry 1 is driven at a preferably constant but adjustable angular speed by the motor 7. The motor 8 is provided for displacing the object, for example, a patient, who is arranged on a patient table in the examination zone 5, parallel to the direction of the rotational axis R or the z axis. These motors 7, 8 are controlled by a control unit 9, for instance, such that the radiation source and the examination zone 5 and, thus, the region of interest within the examination zone move relatively to each other along a helical trajectory. However, it is also possible that the object or the examination zone 5 is not moved, but that only the radiation source 2 is rotated, i.e. that the radiation source moves along a circular trajectory relative to the object or the examination zone 5. Furthermore, in another embodiment, the collimator 3 can be adapted for forming another beam shape, in particular a fan beam, and the detection device 6 can comprise a detection surface, which is shaped corresponding to the other beam shape, in particular to the fan beam.

During a relative movement of the radiation source and the examination zone 5 the detection device 6 acquires projection values depending on the radiation incident on the detection surface of the detection device 6. Therefore, the radiation source 2, the elements for moving the radiation source 2 relative to the examination zone, in particular, the motors 7, 8 and the gantry 1, and the detection device 6 form a projection values acquisition unit for generating acquired projection values of the region of interest.

The acquired projection values are provided to a projection values processing apparatus 1 for processing the acquired projection values. The projection values processing apparatus 10 comprises a receiving unit 12 for receiving the acquired projection values and for providing the acquired projection values to a reconstruction unit 13. The region of interest is located within the examination zone and contains an object or a part of an object. The reconstruction unit reconstructs a first image of the object from the acquired projection values under consideration of reconstruction assumptions. In this embodiment, the reconstruction unit 13 is adapted to reconstruct the first image by using a filtered backprojection. The reconstruction assumptions are, for example, data acquisition on a circular source trajectory with a fan beam and a focus-centered detector, suppression of scattered radiation by anti-scatter grids, correction of X-ray beam intensity variations, and no beam hardening effects. That means the measured projection values can be modeled as line integrals through the object which can be described by monoenergetic X-ray absorption coefficients.

Further possible assumptions are: the object is fully contained inside the reconstructable field of view, the object does not move during data acquisition, the X-ray intensity is high enough so that the noise statistics can be approximated well by a Gaussian distribution.

A two-dimensional filtered backprojection would be a suitable reconstruction algorithm for these assumptions.

The projection values processing apparatus 10 further comprises a simulated projection values determining unit 14 for determining simulated projection values by simulating a projection through the reconstructed first image under consideration of the reconstruction assumptions. In this embodiment, the simulated projection values determining unit is adapted to simulate a forward projection through the reconstructed first image under consideration of the reconstruction assumptions. For each acquired projection value a simulated projection value is determined.

The projection values processing apparatus 10 further comprises an inconsistency determining unit 15 for determining inconsistency values for the acquired projection values, wherein an inconsistency value is indicative of a degree of inconsistency of a respective acquired projection value with the reconstruction assumptions, by comparing the acquired projection values and the simulated projection values. For each pair of acquired projection value and corresponding simulated projection value an inconsistency value is determined.

The inconsistency determining unit 15 comprises a difference determining unit 16 for determining differences between the acquired projection values and the simulated projection values, wherein the inconsistency determining unit 15 is adapted to determine the inconsistency values for the acquired projection values based on differences between the acquired projection values and the simulated projection values. Moreover, the difference determining unit 16 is adapted to determine the differences such that high-frequency components are suppressed. In order to suppress the high-frequency components, in this embodiment, the difference determining unit 16 is adapted to low-pass filter the acquired projection values and to determine the differences by subtracting the respective low-pass filtered acquired projection value and the corresponding simulated projection value from each other. In other embodiments, the difference determining unit can be adapted to determine the differences by subtracting the respective acquired projection value and the corresponding simulated projection value from each other for generating subtraction results and by low-pass filtering the subtraction results. It is also possible that the difference determining unit is adapted to determine the differences by subtracting the respective acquired projection value and the corresponding simulated projection value from each other for generating subtraction results, by reconstructing a subtraction image from the subtraction results determined for the acquired projection values, and by simulating a projection through the reconstructed subtraction image.

The inconsistency determining unit 15 comprises a noise weighting unit 17 for determining a noise value for an acquired projection value and for weighting the determined difference with the inverse of the determined noise value. The noise weighting unit 17 is adapted to weight all differences, which have been determined for the acquired projection values, by the inverse noise values of the respective acquired projection values.

The noise weighting is preferentially determined from the detected intensity of a detector pixel based on calibration data. That means using a reference X-ray source and repeated measurements the noise characteristics for a given system is determined experimentally over a range of X-ray intensities.

The inconsistency determining unit 15 is further adapted to square the weighted differences and to determine the inconsistency values as the squared weighted differences. Thus, for each acquired projection value a squared weighted difference is determined as an inconsistency value. In other embodiments, the square operation and optionally also the weighting operation can be omitted. That means the inconsistency determining unit 15 can be adapted to determine the determined differences with the suppressed high-frequency components as the inconsistency values or to determine the weighted differences with the suppressed high-frequency components as inconsistency values or to determine the squared weighted differences with the suppressed high-frequency components as inconsistency values.

The acquired projection values are assigned to acquisition times. The projection values processing apparatus 10 comprises a temporal inconsistency signal determining unit 18 for determining a temporal inconsistency signal indicative an inconsistency between an acquired projection value and the reconstruction assumption at different times, by assigning the acquisition times to the inconsistency values determined for the acquired projection values of the respective acquisition time. In this embodiment, the temporal inconsistency signal determining unit 18 is adapted to average the inconsistency values belonging to the same acquisition time to generate a one-dimensional temporal inconsistency signal. If a reconstruction assumption is that the object in the examination zone does not move and if the object moves, the temporal inconsistency signal can be regarded as a temporal motion signal indicating the motion of the object. Therefore, the inconsistency values can be used for determining the motion of the object.

The reconstruction unit 13 can be adapted to reconstruct a second image based on the acquired projection values and the determined temporal inconsistency signal. This allows reconstructing a second image having reduced image artifacts caused by inconsistencies between the acquired projection values and the reconstruction assumptions. In this embodiment, a reconstruction assumption, which substantially influences the inconsistency values, is that the object in the region of interest is not moving. The reconstruction unit is therefore adapted to use acquired projection values for reconstructing the second image, which have been acquired at times at which the temporal inconsistency signal shows an inconsistency within a predefined inconsistency range, in particular, at which the temporal inconsistency signal shows a similar inconsistency. Since, in this embodiment, the inconsistency values are mainly influenced by movements of the object, which are not consistent with the reconstruction assumption of a non-moving object, similar inconsistency values indicate similar moving states of the object. The reconstruction unit is therefore adapted to reconstruct an image based on acquired projection values which correspond to the same moving state of the object to be reconstructed.

The reconstruction unit 13 can also be adapted to reconstruct a second image based on acquired projection values only, which have been acquired at a time at which the temporal inconsistency signal shows an inconsistency below a threshold. This ensures that large inconsistencies, i.e. inconsistency values above the threshold, have a reduced effect on the image quality, thereby improving the quality of the second image.

The reconstruction unit 13 can also be adapted to reconstruct a second image of the object from the acquired projection values and the determined inconsistency values for reducing image artifacts caused by inconsistencies between the acquired projection values and the reconstruction assumptions, without using the temporal inconsistency signal. For example, the first image can be reconstructed again with modified reconstruction assumptions based on the same acquired projection values. This modification of the reconstruction assumptions can be performed such that the determined inconsistency values are reduced, in particular, minimized, wherein a final image is reconstructed from the acquired projection values under consideration of the modified reconstruction assumptions. Thus, the reconstruction assumptions can be modified until the inconsistency values are minimized and these modified reconstruction assumptions can be used for reconstructing an image from the acquired projection values, which has an improved image quality.

For example, modified reconstruction assumptions can include a beam hardening correction, i.e. it is assumed that beam hardening is present and the reconstruction algorithm comprises a corresponding beam hardening correction. Another possible modified reconstruction assumption could be that the object moves while acquiring a first part of the projection values and that the object does not move while acquiring a second part of the projection values. The reconstruction algorithm considering the modified reconstruction assumption then preferentially only uses the second part of the acquired projection values for reconstructing an image of the object.

Similar to the above described use of the temporal inconsistency signal, the reconstruction unit 13 can also be adapted to determine acquired projection values having an inconsistency value below a predefined threshold and to use only the acquired projection values having an inconsistency value below the predefined threshold while reconstructing the second image. Moreover, also similar to the above described use of the temporal inconsistency signal, the reconstruction unit 13 can be adapted to determine acquired projection values having similar inconsistency values and to reconstruct an image of the object from the acquired projection values having similar inconsistency values.

The projection values processing apparatus 10 further comprises an inconsistency image determining unit 19 for generating an inconsistency image, wherein for an image element of the inconsistency image inconsistency values which contribute to the respective image element are added. This generation of the inconsistency image is performed by an unfiltered backprojection. This unfiltered backprojection uses preferentially the reconstruction assumptions which have been used by the reconstruction unit 13 for reconstructing the first image.

The inconsistency image determining unit 19 can be adapted to generate the inconsistency image based on inconsistency values being subtraction results with reduced high-frequency components or based on inconsistency values being noise weighted subtraction results with reduced high-frequency components or based on inconsistency values being squared noise weighted subtraction results with suppressed high-frequency components.

The reconstruction unit 13 can be adapted to reconstruct the second image of the object based on the acquired projection values and the determined inconsistency image for reducing image artifacts caused by inconsistencies between the acquired projection values and the reconstruction assumption. For example, the reconstruction assumptions can be modified such that the inconsistencies shown in the inconsistency image are reduced, in particular, the reconstruction assumptions can be optimized such that the inconsistencies shown by the inconsistency image are minimized. An image of the region of interest can then be reconstructed from the acquired projection values by using the optimized reconstruction assumptions.

The projection values processing apparatus 10 further comprises an overlaying unit 20 for overlaying the reconstructed first image and the inconsistency image. This allows directly showing to a user which parts of the first image are affected by image artifacts caused by inconsistencies of the acquired projection values with respect to the reconstruction assumptions. The inconsistency image can also be used to be overlaid over other images like the reconstructed second image.

The projection values processing apparatus 10 further comprises a display unit 11 for displaying the inconsistency values which preferentially form an inconsistency sinogram, the inconsistency image overlaid over the first image or over another reconstructed image like the second image, and a corrected image, i.e. the second image, which has been reconstructed by using the inconsistency values, in particular, the temporal inconsistency signal and/or the inconsistency image.

Also the projection values processing apparatus is preferentially controlled by the control unit 9.

Figure 2:
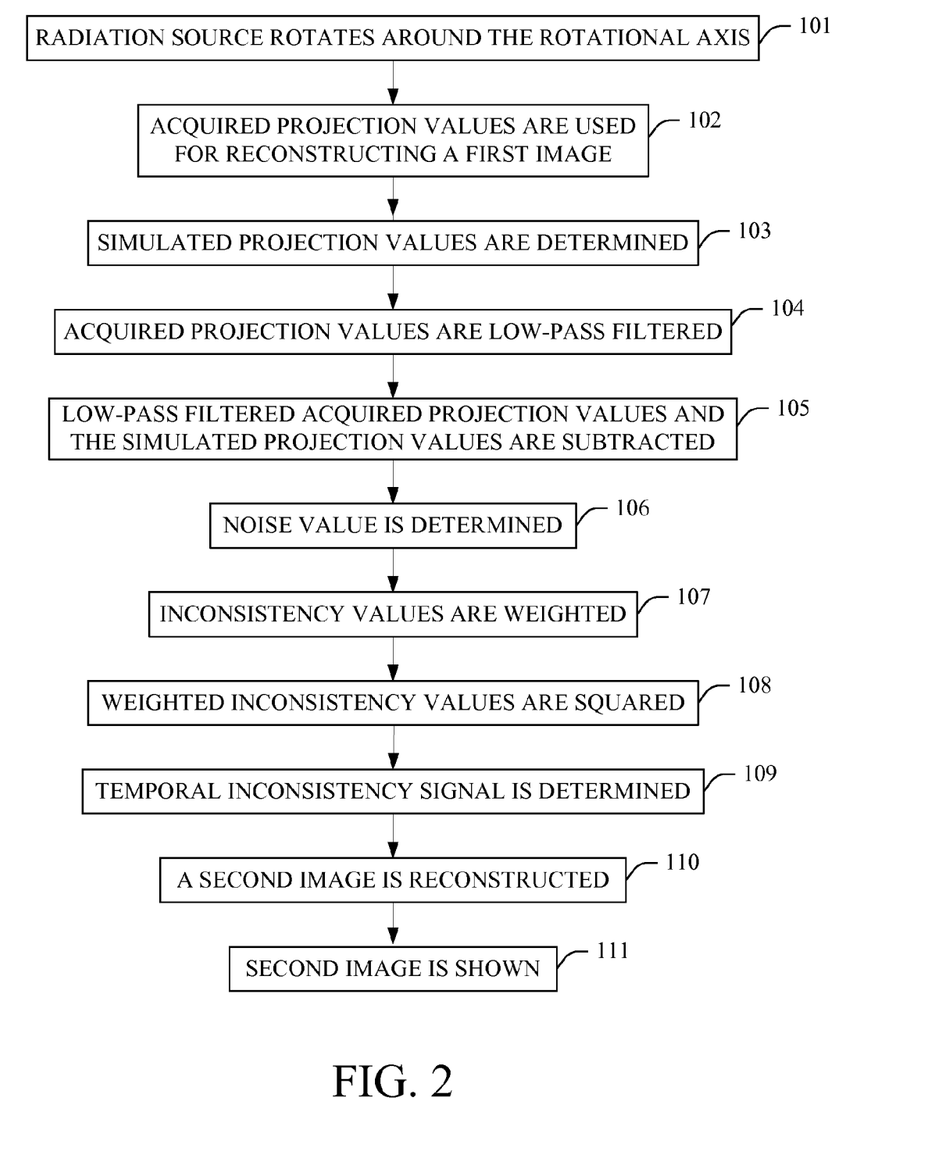
FIG. 2 shows a flowchart exemplarily illustrating an imaging method for imaging a region of interest.

In the following an imaging method for imaging a region of interest will be described with reference to a flowchart shown in FIG. 2.

The imaging method for imaging a region of interest is, in this embodiment, a computed tomography imaging method. In step 101, the radiation source 2 rotates around the rotational axis R and the object or the examination zone 5 is not moved, i.e. the radiation source 2 travels along a circular trajectory around the object or the examination zone 5. In another embodiment, the radiation source 2 can move along another trajectory, for example, a helical trajectory, relative to the object. The radiation source 2 emits radiation traversing the object at least in the region of interest. The radiation, which has traversed the object, is detected by the detection device 6, which generates measured data being projection data.

The acquired projection values are transferred to the projection values processing apparatus 10 and, in step 102 the provided acquired projection values are used for reconstructing a first image of an object in the region of interest under consideration of the reconstruction assumptions. In step 103, simulated projection values are determined by simulating a projection through the reconstructed first image under consideration of the reconstruction assumptions. In step 104, the acquired projection values are low-pass filtered, and in step 105, the low-pass filtered acquired projection values and the simulated projection values are subtracted from each other. The subtraction results, in which high-frequency components have been suppressed, can already be regarded as inconsistency values.

In step 106, for each acquired projection value, i.e. for each inconsistency value, a noise value is determined, and in step 107 the inconsistency values are weighted by the inverse respective noise values. In step 108, the weighted inconsistency values are squared.

In step 109, a temporal inconsistency signal is determined by assigning the acquisition times, at which the acquired projection values have been acquired, to the inconsistency values determined for the acquired projection values of the respective acquisition time. The inconsistency values belonging to the same acquisition time are averaged to generate a one-dimensional temporal inconsistency signal. Instead of averaging the inconsistency values belonging to the same acquisition time the inconsistency values can also simply be summed up. In step 110, a second image is reconstructed based on the acquired projection values and the determined temporal inconsistency signal for reducing image artifacts caused by inconsistencies between the acquired projection data and the reconstruction assumptions. In step 111, the second image is shown on the display unit to a user.

Steps 102 to 111 can be regarded as steps of a projection values processing method. In the projection values processing method steps 109 to 111 can be omitted, i.e. the projection values processing method can be adapted to only determine the inconsistency values. Also the steps 106 to 108 which are related to noise determination, noise weighting and squaring can be omitted. Moreover, the projection values processing method can comprise other steps for using the inconsistency values in other ways as described above in more detail.

Figure 3:
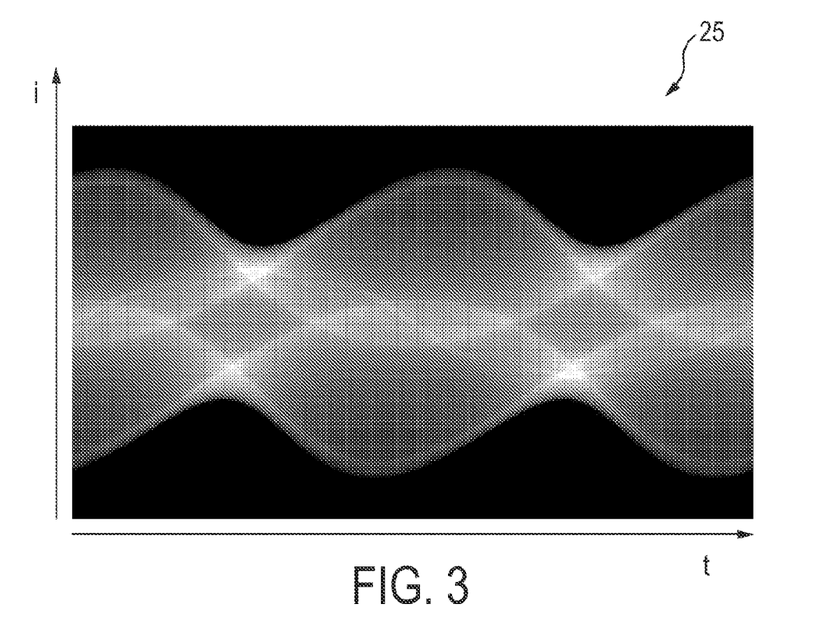
FIG. 3 shows schematically and exemplarily a sinogram of acquired projection values.

FIG. 3 shows schematically and exemplarily a sinogram 25 of acquired projection values. In FIG. 3, the horizontal axis indicates the time t and the vertical axis indicates the i-th acquired projection value measured at the respective time t. The sinogram shown in FIG. 3 is corrupted by motion, i.e. artifacts are induced in the sinogram because of an inconsistency between the acquired projection values, which are influenced by motion of an object in the region on interest, and the reconstruction assumption that motion is not present in the region of interest. The object through which the X-rays have traversed for generating the acquired projection values is, in this embodiment, a thorax phantom in which a small sphere in the center is moving. This movement is only small and the corresponding corruption is therefore not visible in the sinogram shown in FIG. 3.

Figure 4:
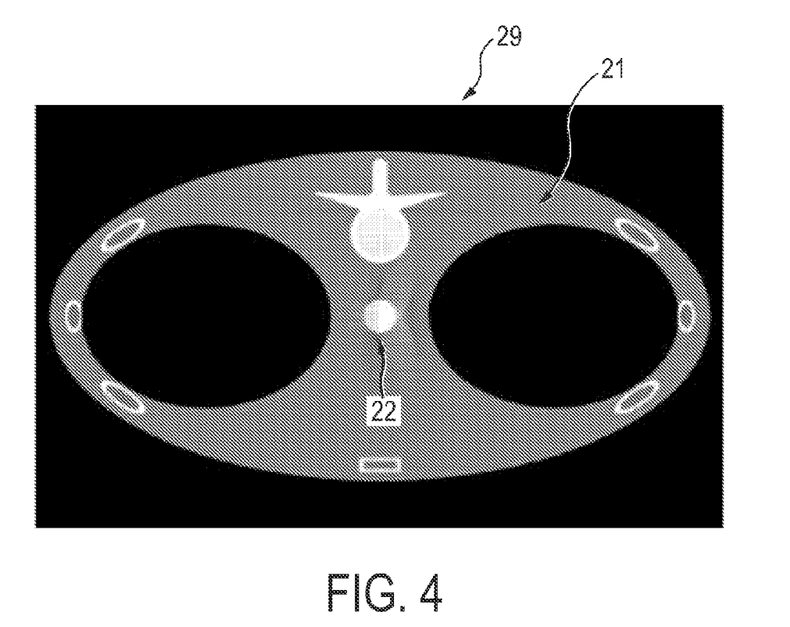
FIG. 4 shows schematically and exemplarily a reconstructed first image which has been reconstructed by using the acquired projection values.

FIG. 4 schematically and exemplarily shows a reconstructed first image 29, which has been reconstructed by using the acquired projection values shown in FIG. 3. A central element 22 within the thorax 21 is moving, thereby causing motion artifacts in the reconstructed first image in the vicinity of the central element 22.

Figure 5:
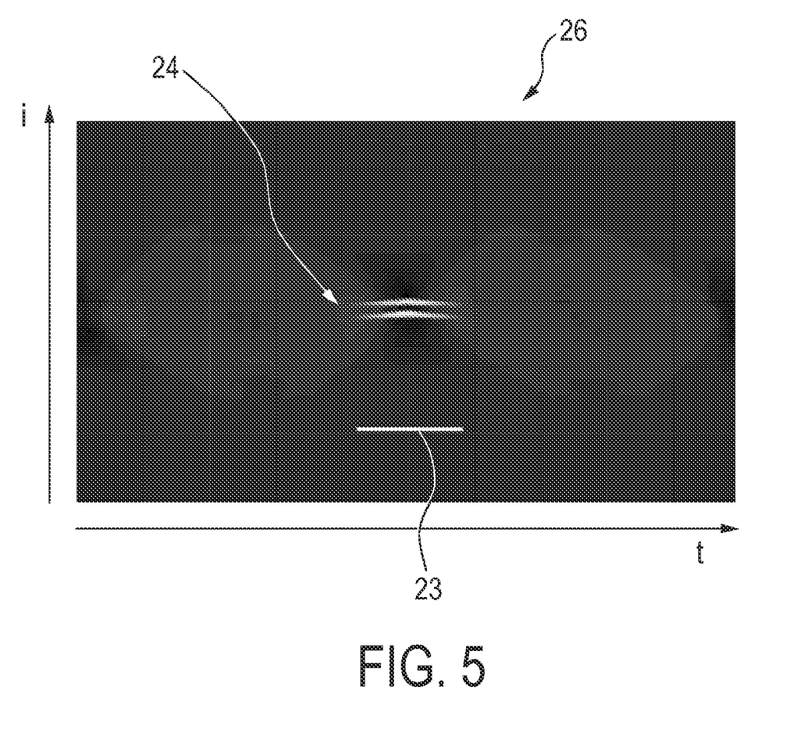
FIG. 5 shows schematically and exemplarily inconsistency values forming an inconsistency sinogram.

FIG. 5 shows schematically and exemplarily inconsistency values which have been determined for the acquired projection values and which form an inconsistency sinogram 26. The inconsistencies shown in FIG. 5 are mainly caused by the motion of the central element 22. Thus, although the corrupted sinogram of the acquired projection values shown in FIG. 3 does not show the corruption by motion, the resulting inconsistency, i.e. the motion, can be detected in the inconsistency sinogram. Therefore, the inconsistency values can be used for determining motion in the region of interest, if a reconstruction assumption is that motion is not present in the region of interest which is reconstructed. The line 23 is not part of the inconsistency sinogram and just indicates the period of motion of the central element 22. As it can been seen in FIG. 5, the duration of the inconsistency values 24 corresponds to the period of motion 23. The structures of the acquired projection values are no longer visible in the inconsistency sinogram shown in FIG. 5.

Figure 6:
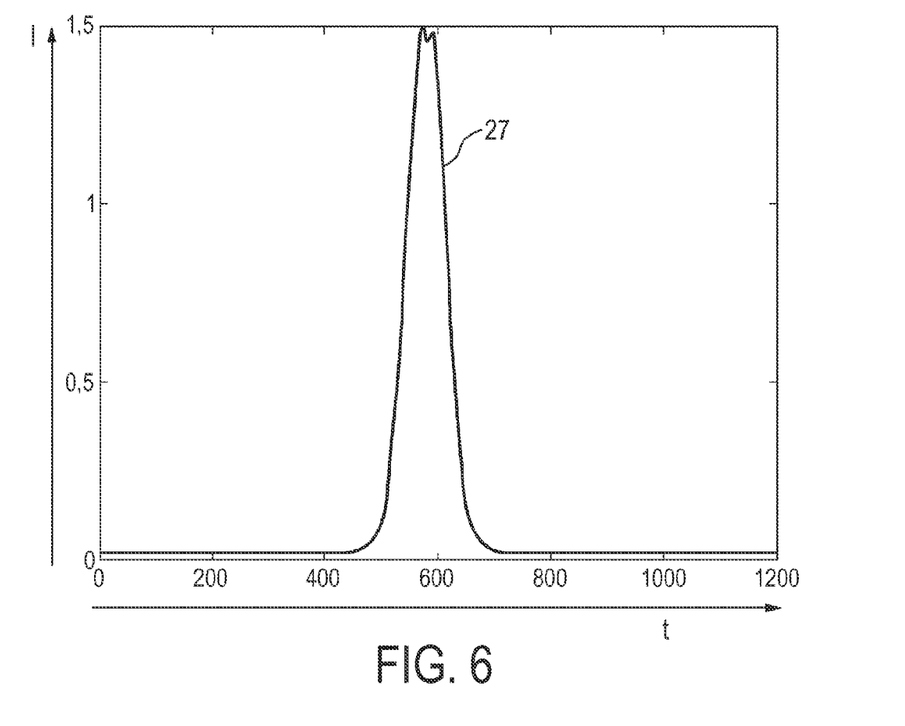
FIG. 6 shows schematically and exemplarily a temporal inconsistency signal being a motion signal.

FIG. 6 shows schematically and exemplarily a temporal inconsistency signal I (t) which has been determined by summing up the inconsistency values shown in FIG. 5, which correspond to the same acquisition time, in arbitrary units. Thus, a one-dimensional temporal inconsistency signal has been generated based on the inconsistency sinogram shown in FIG. 5. The temporal inconsistency signal 27 correlates very well with the actual motion period and shows a very good signal to background ratio.

Figure 7:
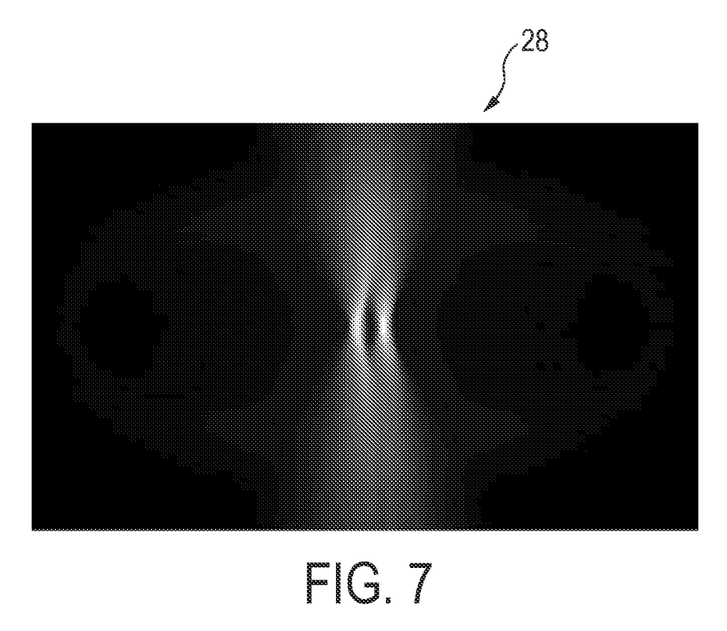
FIG. 7 shows schematically and exemplarily an inconsistency image.

FIG. 7 shows schematically and exemplarily an inconsistency image 28 where large inconsistence, i.e. low confidence, is represented as white. The areas of low confidence coincide with the position of motion artifacts in the reconstructed first image shown in FIG. 4. The inconsistence image shown in FIG. 7 has been generated by an unfiltered back projection of the inconsistency sinogram shown in FIG. 5.

Image reconstruction algorithms for projection values commonly assume that the measured data correspond to line integrals through a stationary object. If this assumption is not fulfilled due to, for example, motion, temporal absorption variation within the object or metal, the reconstructed image shows artifacts. The acquired projection values processing apparatus and method can be applied to the acquired projection values to analyze if the acquired projection values are consistent with the reconstruction assumptions of the reconstruction algorithm. The detected inconsistencies in the acquired projection values, i.e. the inconsistency values, can be used to generate a motion signal, which shows at which time points motion occurred, if a reconstruction assumption is that the object to be reconstructed does not move, and to create an inconsistency image which can also be regarded as a confidence image which shows those voxels of the reconstructed image which are affected by the inconsistency of the acquired projection values, i.e. which shows the position of image artifacts. The information derived from the inconsistency of the acquired projection values can be used in a subsequent image reconstruction which tries to minimize artifacts.

The inconsistency image can be presented to a user like a radiologist as an indication which parts of the image should not be used for diagnostic purposes. The inconsistency image can be adapted such that it shows the probability that the intensity of a voxel is correct. The inconsistency image can therefore also be regarded as confidence image, as already mentioned above, or as a confidence map.

Preferentially, for each acquired projection value the degree of inconsistency is computed, i.e. an inconsistency value is determined. The degree of inconsistency can be used to generate a temporal signal which shows at which time points the inconsistency occurred. This is useful to identify parts of the acquired projection values which belong to the same motion state of the object which can be a patient. For example, unexpected breathing can be detected or the phases of the cardiac cycle can be detected which can be used for reconstructing an image of a heart of a human being or of an animal.

The inconsistency image is essentially a chi-square test for each voxel in the reconstructed image, if the inconsistence image is generated by summing all inconsistency values, which have been noise weighted and squared and which contribute to a given voxel, to compute the chi-square value for this voxel. Using the known properties of the chi-square distribution the resulting value of the respective voxel can be used to compute a probability that the value of this voxel is correct, i.e. that the voxel is not effected by an inconsistency between the acquired projection values and the reconstruction assumption. For the determination of the chi-square distribution it is preferentially assumed that the noise follows a Gaussian distribution. The computed probabilities can form a modified inconsistency image showing the probability that the respective voxel is not affected by the inconsistencies.

Although in the above described embodiments the imaging system is a computed tomography system, in other embodiments, the acquired projection values can be acquired by another imaging modality like a C-arm or a nuclear imaging system like a positron emission tomography system or a single photon emission computed tomography system.

Although in the above described embodiments certain reconstruction assumptions have been used and certain reconstruction assumptions have been modified, in the above mentioned embodiments and also in other embodiments also other reconstruction assumptions can be used for reconstructing an image and can be modified.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Calculations like the reconstruction, the simulation or the determination of the inconsistency values, performed by one or several units or devices can be performed by any other number of units or devices. For example, steps 102 to 110 can be performed by a single unit or by any other number of units. The calculations and/or determinations and/or the control of the imaging system in accordance with the imaging method and/or the control of the projection values processing apparatus in accordance with the projection values processing method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a projection values processing apparatus for processing acquired projection values. A first image is reconstructed from acquired projection values under consideration of a reconstruction assumption by a reconstruction unit. A simulated projection values determining unit determines simulated projection values by simulating a projection through the reconstructed first image under consideration of the reconstruction assumption, and inconsistency values are determined for the acquired projection values by an inconsistency determining unit, wherein an inconsistency value is indicative of a degree of inconsistency of a respective acquired projection value with the reconstruction assumption, by comparing the acquired projection values and the simulated projection values. The inconsistency values can be used for different purposes, for example, improving the quality of a reconstructed image or indicating image elements being affected by an inconsistency between reconstruction assumption and acquired projection values.

The invention claimed is:

1. A projection values processing apparatus for processing acquired projection values, the projection values processing apparatus comprising:
    an acquired projection values providing unit for providing acquired projection values,
    a reconstruction unit for reconstructing a first image from the acquired projection values under consideration of a reconstruction assumption,
    a simulated projection values determining unit for determining simulated projection values by simulating a projection through the reconstructed first image under consideration of the reconstruction assumption,
    a difference determining unit for determining differences between the acquired projection values and simulated projection values by subtracting the respective acquired projection value and the simulated projection value corresponding to the respective acquired projection value from each other for generating subtraction result, reconstructing a subtraction image from the subtraction results determined for the acquired projection values, and simulating a projection through the reconstructed subtraction image,
    an inconsistency determining unit for determining inconsistency values for the acquired projection values, wherein an inconsistency value is indicative of a degree of inconsistency of a respective acquired projection value with the reconstruction assumption based on the determined differences.

2. The projection values processing apparatus as defined in claim 1, wherein the difference determining unit is adapted to determine the differences such that a high-frequency component of the differences is more suppressed than a low-frequency component of the differences.

3. The projection values processing apparatus as defined in claim 2, wherein the difference determining unit is adapted to low-pass filter the acquired projection values and to determine the differences by subtracting the respective low-pass filtered acquired projection value and the simulated projection value corresponding to the respective acquired projection value from each other.

4. The projection values processing apparatus as defined in claim 2, wherein the difference determining unit is adapted to determine the differences by subtracting the respective acquired projection value and the simulated projection value corresponding to the respective acquired projection value from each other for generating subtraction results and by low-pass filtering the subtraction results.

5. The projection values processing apparatus as defined in claim 2, wherein the inconsistency determining unit further comprises a noise weighting unit for determining a noise value for an acquired projection value and for weighting the determined difference with the inverse of the determined noise value, wherein the inconsistency determining unit is adapted to determine the inconsistency value for an acquired projection value based on the weighted difference.

6. The projection values processing apparatus as defined in claim 5, wherein the inconsistency determining unit is adapted to square the weighted difference and to determine an inconsistency value based on the squared weighted difference.

7. The projection values processing apparatus as defined in claim 1, wherein the acquired projection values have been assigned to acquisition times, wherein the projection values processing apparatus further comprises a temporal inconsistency signal determining unit by assigning the acquisition times to the inconsistency values determined for the acquired projection values of the respective acquisition time.

8. The projection values processing apparatus as defined in claim 1, wherein the projection values processing apparatus further comprises an inconsistency image determining unit for generating an inconsistency image, wherein for an image element of the inconsistency image inconsistency values which contribute to the respective image element are added.

9. The projection values processing apparatus as defined in claim 8, wherein the projection values processing apparatus further comprises an overlaying unit for overlaying the reconstructed first image and the inconsistency image.

10. The projection values processing apparatus as defined in claim 1, wherein the reconstruction unit is adapted to reconstruct a second image of the object from the acquired projection values and the determined inconsistency values for reducing image artifacts caused by inconsistencies between the acquired projection values and the reconstruction assumption.

11. An imaging system for imaging a region of interest, the imaging system comprising:
    a projection values acquisition unit for acquiring projection values of the region of interest, and
    a projection values processing apparatus for processing acquired projection values as defined in claim 1.

12. A projection values processing method for processing acquired projection values, the projection values processing method comprising following steps:
    providing acquired projection values, wherein the acquired projection values are assigned to acquisition times,
    reconstructing a first image from the acquired projection values under consideration of a reconstruction assumption,
    determining simulated projection values by simulating a projection through the reconstructed first image under consideration of the reconstruction assumption, and
    determining inconsistency values for the acquired projection values, wherein an inconsistency value is indicative of a degree of inconsistency of a respective acquired projection value with the reconstruction assumption, by comparing the acquired projection values and the simulated projection values;
    determining a temporal inconsistency signal by assigning the acquisition times to the inconsistency values determined for the acquired projection values of the respective acquisition time.

13. A non-statutory computer storage medium encoded with a computer program for processing acquired projection values, which, when executed by a computer processor cause the computer processor to:
    provide acquired projection values,
    reconstruct a first image from the acquired projection values under consideration of a reconstruction assumption,
    determine simulated projection values by simulating a projection through the reconstructed first image under consideration of the reconstruction assumption,
    determine inconsistency values for the acquired projection values by comparing the acquired projection values and the simulated projection values, wherein an inconsistency value is indicative of a degree of inconsistency of a respective acquired projection value with the reconstruction assumption, and
    generate an inconsistency image, by adding, for an image element of the inconsistency image, inconsistency values which contribute to the respective image element.

14. A projection values processing apparatus for processing acquired projection values, the projection values processing apparatus comprising:
    an acquired projection values providing unit for providing acquired projection values,
    a reconstruction unit for reconstructing a first image from the acquired projection values under consideration of a reconstruction assumption,
    a simulated projection values determining unit for determining simulated projection values by simulating a projection through the reconstructed first image under consideration of the reconstruction assumption,
    a difference determining unit for determining differences between the acquired projection values and simulated projection values,
    a noise weighting unit for determining a noise value for an acquired projection value and for weighting the determined difference with the inverse of the determined noise value, and
    an inconsistency determining unit for determining inconsistency values for the acquired projection values based on the weighted differences, wherein an inconsistency value is indicative of a degree of inconsistency of a respective acquired projection value with the reconstruction assumption.

15. The projection values processing apparatus as defined in claim 14, wherein the difference determining unit is adapted to determine the differences by subtracting the respective acquired projection value and the simulated projection value corresponding to the respective acquired projection value from each other for generating subtraction results, by reconstructing a subtraction image from the subtraction results determined for the acquired projection values, and by simulating a projection through the reconstructed subtraction image.

16. The projection values processing apparatus as defined in claim 14, wherein the acquired projection values have been assigned to acquisition times, wherein the projection values processing apparatus further comprises a temporal inconsistency signal determining unit by assigning the acquisition times to the inconsistency values determined for the acquired projection values of the respective acquisition time.

17. The projection values processing apparatus as defined in claim 14, wherein the projection values processing apparatus further comprises an inconsistency image determining unit for generating an inconsistency image, wherein for an image element of the inconsistency image inconsistency values which contribute to the respective image element are added.

* * * * *